United States Patent
Stout et al.

(10) Patent No.: US 9,891,144 B2
(45) Date of Patent: Feb. 13, 2018

(54) FLUID SAMPLER WITH CONFIRMATION FEEDBACK

(71) Applicant: L.B. Foster Company, Pittsburgh, PA (US)

(72) Inventors: Marc C. Stout, Conroe, TX (US); Milton E. Page, Willis, TX (US)

(73) Assignee: L. B. Foster Company, Pittsburgh, PA (US)

( * ) Notice: Subject to any disclaimer, the term of this patent is extended or adjusted under 35 U.S.C. 154(b) by 0 days.

(21) Appl. No.: 15/294,421

(22) Filed: Oct. 14, 2016

(65) Prior Publication Data

US 2017/0108413 A1    Apr. 20, 2017

Related U.S. Application Data

(60) Provisional application No. 62/241,679, filed on Oct. 14, 2015.

(51) Int. Cl.
*G01N 1/20* (2006.01)

(52) U.S. Cl.
CPC ... *G01N 1/2042* (2013.01); *G01N 2001/2057* (2013.01)

(58) Field of Classification Search
USPC ............................. 73/864.34, 863.11, 73.41
See application file for complete search history.

(56) References Cited

U.S. PATENT DOCUMENTS

| | | | | |
|---|---|---|---|---|
| 4,207,030 A * | 6/1980 | Pearson | ................. | G01F 23/16 200/183 |
| 4,238,290 A * | 12/1980 | Schabert | ................. | G21C 9/00 376/250 |
| 5,109,710 A * | 5/1992 | Newkirk | ................. | G01N 30/12 73/23.41 |
| 5,114,439 A * | 5/1992 | Yost | ...................... | G01N 30/30 95/18 |
| 5,614,089 A * | 3/1997 | Allington | ........... | B01D 11/0203 210/198.2 |
| 5,741,960 A * | 4/1998 | Payne | ................. | G01N 1/2035 422/89 |
| 7,894,840 B2 * | 2/2011 | Ito | ........................ | H04W 36/18 455/509 |
| 8,367,413 B2 * | 2/2013 | Jones | ..................... | G01N 30/88 436/161 |
| 2006/0184069 A1 * | 8/2006 | Vaitekunas | ............. | A61N 7/02 601/2 |

* cited by examiner

*Primary Examiner* — Jewel V Thompson
(74) *Attorney, Agent, or Firm* — Paul D. Bangor, Jr.; Clark Hill, PLC

(57) ABSTRACT

A positive pressure displacement fluid sampler, comprising: a sample probe disposed in a sample probe connection; a needle valve in communication with the sample probe; a three-way solenoid valve disposed between the needle valve, a sample collection body and a sample collection tank; an adjustment stem for adjusting the size of the sample to be collected on each draw; and a confirmation switch for sending an electronic or other type signal for confirming that a sample or samples have actually been collected at prescribed times and/or frequencies. The displacement sampler may be spring-loaded and the confirmation switch may comprise a radio transmitter.

2 Claims, 2 Drawing Sheets

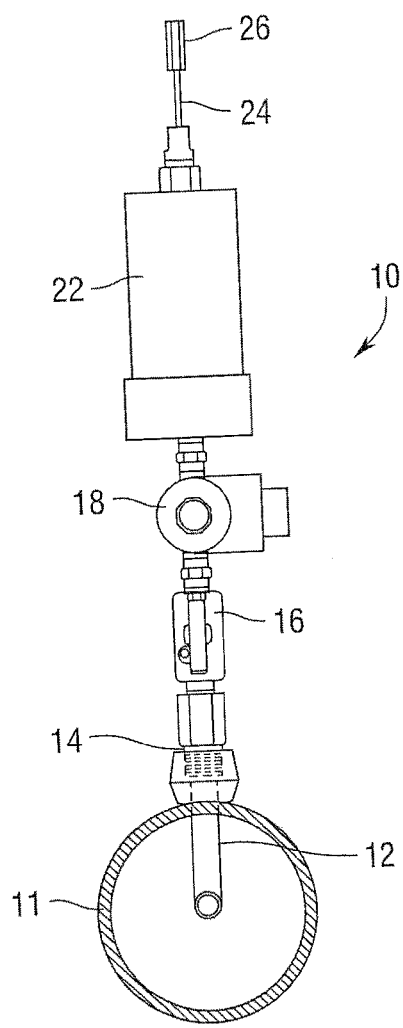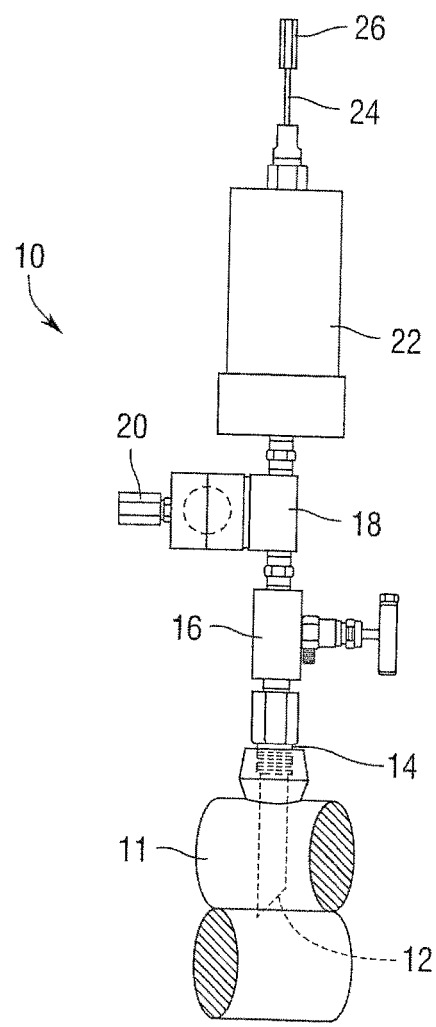
Fig.2
Fig.3

FLUID SAMPLER WITH CONFIRMATION FEEDBACK

CROSS REFERENCE TO RELATED APPLICATIONS

This application claims the benefit of the filing date of U.S. provisional patent application Ser. No. 62/241,679, filed on Oct. 14, 2015, the entirety of which is incorporated herein by reference for all purposes.

TECHNICAL FIELD

The present disclosure relates to fluid sampling devices, and more particularly to a device for sampling fluids under pressure in a pipeline, tube, duct, conduit, or the like.

BACKGROUND OF THE DISCLOSURE

Fluids flowing through pipelines or tubes often need to be sampled to determine the composition of the fluid being transported. For example, payments for oil or gas delivered from a pipeline may depend on various characteristics of the oil or gas transported through the line. It is desirable to be able to sample the fluid in the pipeline easily and repeatedly without opening the pipeline, which is often under pressure. Because the composition of the transported fluid often varies with time, it is particularly important that the samples are actually collected at various times as may be required.

Thus there is a need for a device that permits removal of samples from pipelines, tubes, and the like without opening them while providing confirmation that actual samples have been collected at the prescribed times and frequencies.

Some conventional sampling systems have two pistons in a common passageway, with one having a tubular shaft mounted coaxially on the solid shaft of the other. This passageway is a side passageway through which fluid is only intended to flow during sampling. This side passageway intersects a main flow passageway, which is being sampled. The piston closest to the main passageway moves out of the side passageway and into the main passageway to expose the space in the side passageway between the pistons to the fluid sample. The piston furthest from the main passageway allows flow into, but blocks flow through, the side passageway. Then both pistons are simultaneously drawn into the side passageway in a spaced relationship to capture a sample in the annular space in the side passageway between the pistons. The pistons are aligned with a lateral port in the side passageway and moved toward each other to force a sample of fluid out through the port. There is no continuous fluid flow through the side passageway, as the side passageway is either open only to the main passageway, open only to the outlet port, or open to neither outlet port nor main passageway.

Another prior sampling system has lateral inlets and outlets to a sampling passageway between the inlets and outlets. This has no pistons, the sampling being done by pressure responsive valve timers. This method results in a variable quantity of sample depending on pressure in the line being sampled, and depends on the pressure in the sample container being lower than that in the line being sampled. At least three separate pressure responsive valves and a lengthy sample line are required.

SUMMARY

One aspect of a preferred embodiment of the present disclosure comprises a positive pressure displacement fluid sampler, comprising: a sample probe disposed in a sample probe connection; a needle valve in communication with the sample probe; a three-way solenoid valve disposed between the needle valve, a sample collection body and a sample collection tank; an adjustment stem for adjusting the size of the sample to be collected on each draw; and a confirmation switch for sending an electronic or other type signal for confirming that a sample or samples have actually been collected at prescribed times and/or frequencies.

In another aspect of a preferred displacement fluid sampler of the present disclosure, the displacement sampler is spring-loaded.

In a further aspect of a preferred displacement fluid sampler of the present disclosure, the confirmation switch comprises a radio transmitter.

BRIEF DESCRIPTION OF THE DRAWINGS

The present disclosure is illustrated by way of example and not limitation in the figures of the accompanying drawings, in which:

FIG. 2 is a plan view of a preferred embodiment of a displacement fluid sampler according to the present disclosure; and FIG. 3 is a side elevational view of a preferred embodiment of a displacement fluid sampler according to the present disclosure.

DETAILED DESCRIPTION

Figure 1:
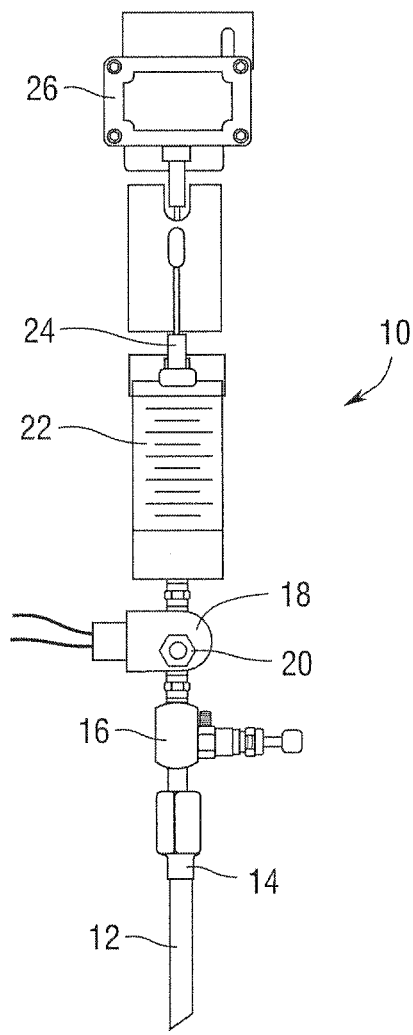
FIG. 1 is a front elevational view of a preferred embodiment of a displacement fluid sampler according to the present disclosure.

In the following detailed description, reference is made to the accompanying examples and figures that form a part hereof, and in which is shown by way of illustration specific embodiments in which the inventive subject matter may be practiced. These embodiments are described in sufficient detail to enable those skilled in the art to practice them, and it is to be understood that other embodiments may be utilized and that structural, logical, and electrical changes may be made without departing from the scope of the inventive subject matter. Such embodiments of the inventive subject matter may be referred to, individually and/or collectively, herein by the term "disclosure" merely for convenience and without intending to voluntarily limit the scope of this application to any single disclosure or inventive concept if more than one is in fact disclosed.

The following description is, therefore, not to be taken in a limited sense, and the scope of this disclosure is defined by the appended claims.

A preferred fluid sampler 10 of the present disclosure is a spring loaded positive displacement sampler utilizing a piston/cylinder assembly, preferably within body 22. Fluid sampler 10 of the present disclosure offers several advantages over traditional diaphragm samplers while still offering a low cost solution for sampling. Because it has no diaphragm, fluid sampler 10 eliminates common component failures associated therewith. Fluid sampler 10 comprises a stainless steel body, electric three-way solenoid valve 18, needle valve 16, and inlet probe 12 for drawing sample from pipe or tank 11. Preferably a confirmation switch 26 can be used to send a confirmation signal at the completion of each sample.

Preferred fluid sampler 10 is designed to extract samples from 1-22 cubic centimeters. Adjusting the sample size is preferably accomplished via a threaded adjustment stem 24.

Fluid sampler 10 preferably is activated by an external signal. This signal, which energizes solenoid 18, allows samples to enter the sampler body 22 via the inlet probe 12. Once the sampler body 22 is filled and the solenoid valve 18 is de-energized, the sample is discharged into an external sample container via outlet valve 20.

It should be understood that while this disclosure has been described herein in terms of specific, preferred embodiments set forth in detail, such embodiments are presented by way of illustration of the general principles of the disclosure, and the disclosure is not necessarily limited thereto. Certain modifications and variations in any given material, process step or chemical formula will be readily apparent to those skilled in the art without departing from the true spirit and scope of the present disclosure, and all such modifications and variations should be considered within the scope of the claims that follow.

What is claimed is:

1. A positive pressure displacement fluid sampler, comprising:
    a sample probe disposed in a sample probe connection;
    a needle valve in communication with the sample probe;
    a three-way solenoid valve disposed between the needle valve, a sample collection body and a sample collection tank;
    an adjustment stem for adjusting the size of the sample to be collected on each draw; and
    a confirmation switch for sending an electronic or other type signal for confirming that a sample or samples have actually been collected at prescribed times and/or frequencies; wherein the displacement sampler is spring-loaded.

2. A positive pressure displacement fluid sampler, comprising:
    a sample probe disposed in a sample probe connection;
    a needle valve in communication with the sample probe;
    a three-way solenoid valve disposed between the needle valve, a sample collection body and a sample collection tank;
    an adjustment stem for adjusting the size of the sample to be collected on each draw; and
    a confirmation switch for sending an electronic or other type signal for confirming that a sample or samples have actually been collected at prescribed times and/or frequencies, wherein the confirmation switch comprises a radio transmitter.

* * * * *